US010200635B2

(12) United States Patent
Hunt et al.

(10) Patent No.: US 10,200,635 B2
(45) Date of Patent: *Feb. 5, 2019

(54) ACTIVE REAL-TIME CHARACTERIZATION SYSTEM

(71) Applicant: The Boeing Company, Chicago, IL (US)

(72) Inventors: Jeffrey H. Hunt, Thousand Oaks, CA (US); John H. Belk, St. Louis, MO (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/711,626

(22) Filed: Sep. 21, 2017

(65) Prior Publication Data

US 2018/0013964 A1 Jan. 11, 2018

Related U.S. Application Data

(63) Continuation of application No. 14/526,246, filed on Oct. 28, 2014, now Pat. No. 9,787,916.

(51) Int. Cl.
*H04N 5/33* (2006.01)
*G01N 21/88* (2006.01)
*G01N 21/95* (2006.01)
*H04N 5/225* (2006.01)
(Continued)

(52) U.S. Cl.
CPC ............... *H04N 5/332* (2013.01); *B64F 5/60* (2017.01); *G01N 21/8806* (2013.01); *G01N 21/95* (2013.01); *H04N 5/2256* (2013.01);

*G01N 2021/8472* (2013.01); *G01N 2021/8845* (2013.01); *G01N 2201/0683* (2013.01)

(58) Field of Classification Search
CPC ........ H04N 5/332; H04N 5/2256; B64F 5/60; G01N 21/8806; G01N 21/95
See application file for complete search history.

(56) References Cited

U.S. PATENT DOCUMENTS 5,973,778 A * 10/1999 Hunt ................. G01N 21/55
356/237.2
6,781,686 B2 * 8/2004 Hunt ................. G01N 21/17
250/559.4
6,788,405 B2 9/2004 Hunt
(Continued)

*Primary Examiner* — Anner N Holder
*Assistant Examiner* — Hesham K Abouzahra
(74) *Attorney, Agent, or Firm* — Toler Law Group, P.C.

(57) ABSTRACT

A system for providing active real-time characterization of an article under test is disclosed. An infrared light source, a first visible light source and a second visible light source each outputs and directs a beam of coherent light at a particular area on the article under test. A visible light camera and a visible light second harmonic generation camera, an infrared camera and an infrared second harmonic generation camera, a sum frequency camera and a third order camera are each configured to receive a respective predetermined return beam of light from the particular area on the article under test. A processor receives signals from the cameras and calculates in real time respective spectroscopic signals and compares each calculated signal with each other calculated signal and with a predetermined baseline signal to ensure that the article under test conforms to an expected value.

20 Claims, 4 Drawing Sheets

(51) Int. Cl.
*B64F 5/60* (2017.01)
*G01N 21/84* (2006.01)

(56) References Cited

U.S. PATENT DOCUMENTS

| | | | |
|---|---|---|---|
| 6,795,175 B2 | 9/2004 | Hunt | |
| 6,798,502 B2 | 9/2004 | Hunt | |
| 6,819,844 B2* | 11/2004 | Hunt | G01N 21/17 |
| | | | 356/300 |
| 7,289,656 B2* | 10/2007 | Engelbart | G01N 21/95 |
| | | | 382/141 |
| 7,304,305 B2 | 12/2007 | Hunt | |
| 7,757,558 B2 | 7/2010 | Bossie et al. | |
| 7,983,469 B2 | 7/2011 | Engelbart et al. | |
| 8,664,583 B2 | 3/2014 | Hunt et al. | |
| 8,789,837 B2 | 7/2014 | Chang et al. | |
| 9,151,941 B2* | 10/2015 | Fresquet | G01B 9/04 |
| 2003/0231302 A1* | 12/2003 | Hunt | G01N 21/94 |
| | | | 356/237.2 |
| 2003/0234360 A1* | 12/2003 | Hunt | G01N 21/3563 |
| | | | 250/339.06 |
| 2006/0039423 A1* | 2/2006 | Tokuhisa | G02F 1/353 |
| | | | 372/22 |
| 2013/0048841 A1 | 2/2013 | Hunt et al. | |
| 2013/0050685 A1 | 2/2013 | Hunt et al. | |
| 2013/0170509 A1* | 7/2013 | Tokuhisa | H01S 3/0092 |
| | | | 372/5 |

* cited by examiner

ACTIVE REAL-TIME CHARACTERIZATION SYSTEM

RELATED APPLICATION

This patent arises from a continuation of U.S. patent application Ser. No. 14/526,246 (now U.S. Pat. No. 9,787, 916), filed Oct. 28, 2014, entitled "Active Real-Time Characterization System," which is hereby incorporated by reference in its entirety.

FIELD

This disclosure relates generally to an active real-time characterization system for use during composite overlay manufacturing.

BACKGROUND

In recent years, aircraft manufacturers have developed aircraft designs and aircraft fabrication methods that make greater use of carbon fiber composite materials and the like ("composite materials" or "CFCM"), such as graphite/epoxy, carbon fiber reinforced plastic ("CFRP") and graphite reinforced polymer ("GRP"). Composite materials are significantly lighter than traditional aircraft materials (e.g. aluminum, titanium, steel and alloys thereof), and can provide high strength with low weight, allowing lighter, more fuel efficient aircraft. In some newer aircraft, for example, the majority of the primary structure, including the fuselage and wing, is made of composite materials. One drawback in the growing use of carbon fiber composite materials is the lack of effective non-destructive evaluation type testing methodologies available for testing such materials during and after manufacture. In particular, there is a lack non-destructive evaluation type testing systems for providing real time characterization of composites during overlay manufacturing.

Accordingly, there is a need for a testing system which addresses the drawbacks identified above.

SUMMARY

In a first aspect, a system for providing active real-time characterization of an article under test is disclosed. An infrared light source outputs a beam of coherent infrared light. The infrared light source is configured to direct the beam of coherent infrared light at a particular area on the article under test. A first visible light source outputs a first beam of coherent visible light. The first visible light source is configured to direct the first beam of coherent visible light at the same particular area on the article under test. A visible light camera and a visible light second harmonic generation camera each configured to receive a first predetermined return beam of light from the particular area on the article under test. An infrared camera and an infrared second harmonic generation camera are each configured to receive a second predetermined return beam of light from the particular area on the article under test. A sum frequency camera is configured to receive a third return beam of light from the particular area on the article under test. A processor is coupled to receive signals from the visible light camera, the visible light second harmonic generation camera, the infrared camera, the infrared second harmonic generation camera and the sum frequency camera. The processor is configured to calculate in real time a linear spectroscopic signal, a second harmonic generation spectroscopic signal and a sum-frequency spectroscopic signal. The processor is also configured to compare each calculated signal with each other calculated signal and with a predetermined baseline signal to ensure that the article under test conforms to an expected value.

In a further embodiment, a second visible light source may output a second beam of coherent visible light. The second visible light source may be configured to direct the second beam of coherent visible light at the same particular area on the article under test. A third order camera may be configured to receive a fourth return beam of light from the particular area on the article under test. In this further embodiment, the processor may also be configured to calculate in real time a third order spectroscopic signal and to compare the third order spectroscopic signal with the other calculated signals and with a predetermined baseline signal to ensure that the article under test conforms to an expected value.

In a second aspect, a system for providing active real-time characterization of an article under test is disclosed. An infrared light source outputs a beam of coherent infrared light. The infrared light source is configured to direct the beam of coherent infrared light at a particular area on the article under test. A first visible light source outputs a first beam of coherent visible light. The first visible light source is configured to direct the first beam of coherent visible light at the same particular area on the article under test. A visible light camera and a visible light second harmonic generation camera are each configured to receive a first predetermined return beam of light from the particular area on the article under test. An infrared camera and an infrared second harmonic generation camera are each configured to receive a second predetermined return beam of light from the particular area on the article under test. A third order camera is configured to receive a third return beam of light from the particular area on the article under test. A processor is coupled to receive signals from the visible light camera, the visible light second harmonic generation camera, the infrared camera, the infrared second harmonic generation camera and the third order camera. The processor is configured to calculate in real time a linear spectroscopic signal, a second harmonic generation spectroscopic signal and a third order spectroscopic signal. The processor is also configured to compare each calculated signal with each other calculated signal and with a predetermined baseline signal to ensure that the article under test conforms to an expected value.

In a further embodiment, a second visible light source may output a second beam of coherent visible light. The second visible light source may be configured to direct the second beam of coherent visible light at the same particular area on the article under test. A sum frequency camera may be configured to receive a fourth return beam of light from the particular area on the article under test. The processor may also be configured to calculate in real time a sum frequency spectroscopic signal and to compare the sum frequency spectroscopic signal with the other calculated signals and with a predetermined baseline signal to ensure that the article under test conforms to an expected value.

In either aspect, each of the sources may include an intensity control for setting a predetermined intensity for the respective output beam of light, a frequency control for setting a predetermined wavelength for the respective output beam of light, and a polarization control for setting a predetermined polarization for the respective output beam of light. Further, in either aspect, each of the cameras may include an intensity control for setting a predetermined intensity for the respective input beam of light, a frequency control for setting a predetermined wavelength for the respective input beam of light, and a polarization control for setting a predetermined polarization for the respective input beam of light. Finally, in ether aspect, the system may further include a beam splitter configured to split a return beam of light into two portions, a first portion directed to the visible light camera and a second portion directed to the visible light second harmonic generation camera.

In a still further aspect, a method for active real-time characterization of an article under test. An infrared light source and a first visible light source are directed at an area on a surface of the article under test. A visible light camera, a visible light second harmonic generation camera, an infrared camera, an infrared second harmonic generation camera and a sum-frequency camera are aligned to receive light from the infrared light source and first visible light source reflected from the surface of the article under test. Data is acquired from each of the cameras based on the received light. The data from each of the cameras is compared and contrasted, and correlations among the data are observed. Finally, the correlations among the data are analyzed and interpreted to determine if the composition of the article under test is within expected ranges. In a further embodiment, a second visible light source is also directed at the area on a surface of the article under test, a third order camera is aligned to receive light from the first visible light source and the second visible light source reflected from the surface of the article under test, and the data from the third order camera is acquired, analyzed and used to determine if the composition of the article under test is within expected ranges.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

Figure 1:
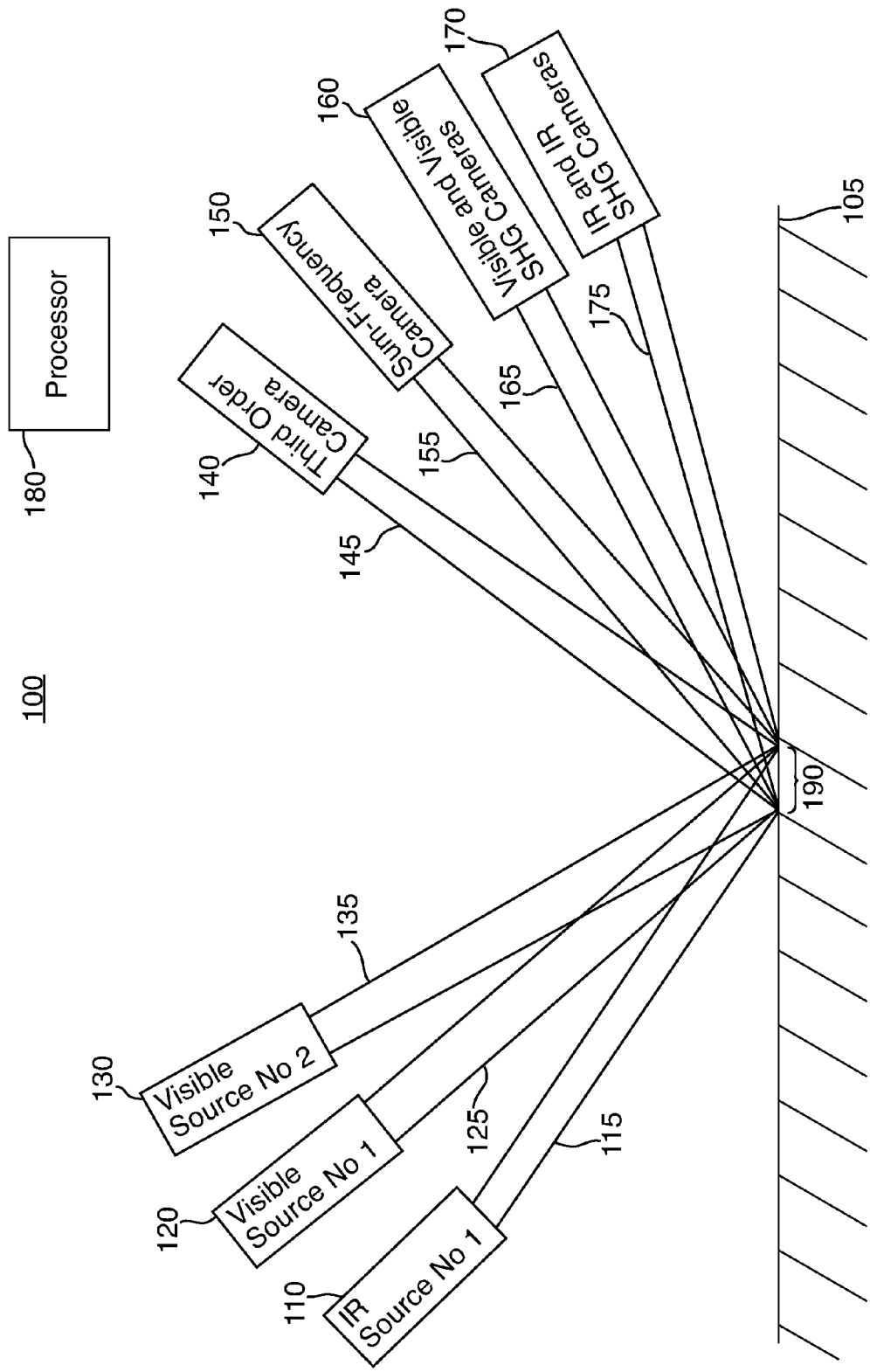
FIG. 1 is a block diagram of an active real-time characterization system for use during composite overlay manufacturing according to an aspect of the present disclosure.

Referring now to FIG. 1, the active real-time characterization system 100 of the present disclosure includes an infrared (IR) light source 110, a first visible light source 120 and a second visible light source 130. Each of the light sources 110, 120, 130 is positioned to direct a beam of coherent light at an area 190 on a surface of an article under test 105, e.g., a part constructed from carbon-fiber composites. In particular, IR source 110 is positioned to direct a coherent beam of light 115 at area 190, first visible light source 120 is positioned to direct a coherent beam of light 125 at area 190, and send visible light source 130 is positioned to direct a coherent beam of light 135 at area 190. The beams 115, 125, 135 may be emitted directly from the respective light sources 110, 120, 130 or may be emitted via respective optical fibers (and appropriate lenses, etc.) coupled to the light sources 110, 120, 130. When beams 115, 125, 135 are emitted via respective optical fibers, each light source 110, 120 130 consists of a laser of the appropriate type (visible or IR light) that is coupled to an input of an associated optical fiber via input optics. The laser is preferably a solid state laser or a diode laser and may be, for example, a pulsed diode laser, a continuous-wave diode laser, a pulsed solid state laser, a continuous-wave solid state laser, a flash-lamp pumped solid state laser, or a diode pumped solid state laser. The input optics consist of an input polarizer, an input wavelength discriminator, an input spatial filter and an input propagation optics. The input polarizer is, for example, a Brewster angle polarizer, a thin film polarizer, a Glan-air or Glan-Thompson polarizer or other crystal polarizer. The wavelength discriminator is, for example, a color filter, a dielectric film, a holographic transmission filter, or a grating. The input propagation optics is formed of one or more refractive or reflective optics which, when used in combination, control the divergence or convergence of the beam as it propagates towards the first input optical fiber. The input optics are optimized for the wavelength of the associated optical source. Coupling optics are coupled to an output of each optical fiber to direct the beam to area 190. IR light source 110 is configured to output light at a fixed, predetermined IR wavelength, while first visible light source 120 is configured to output light at a first fixed, predetermined visible wavelength and second visible light source 130 is configured to output light at a second fixed, predetermined visible wavelength, different from the first fixed, predetermined visible wavelength.

Figure 2:
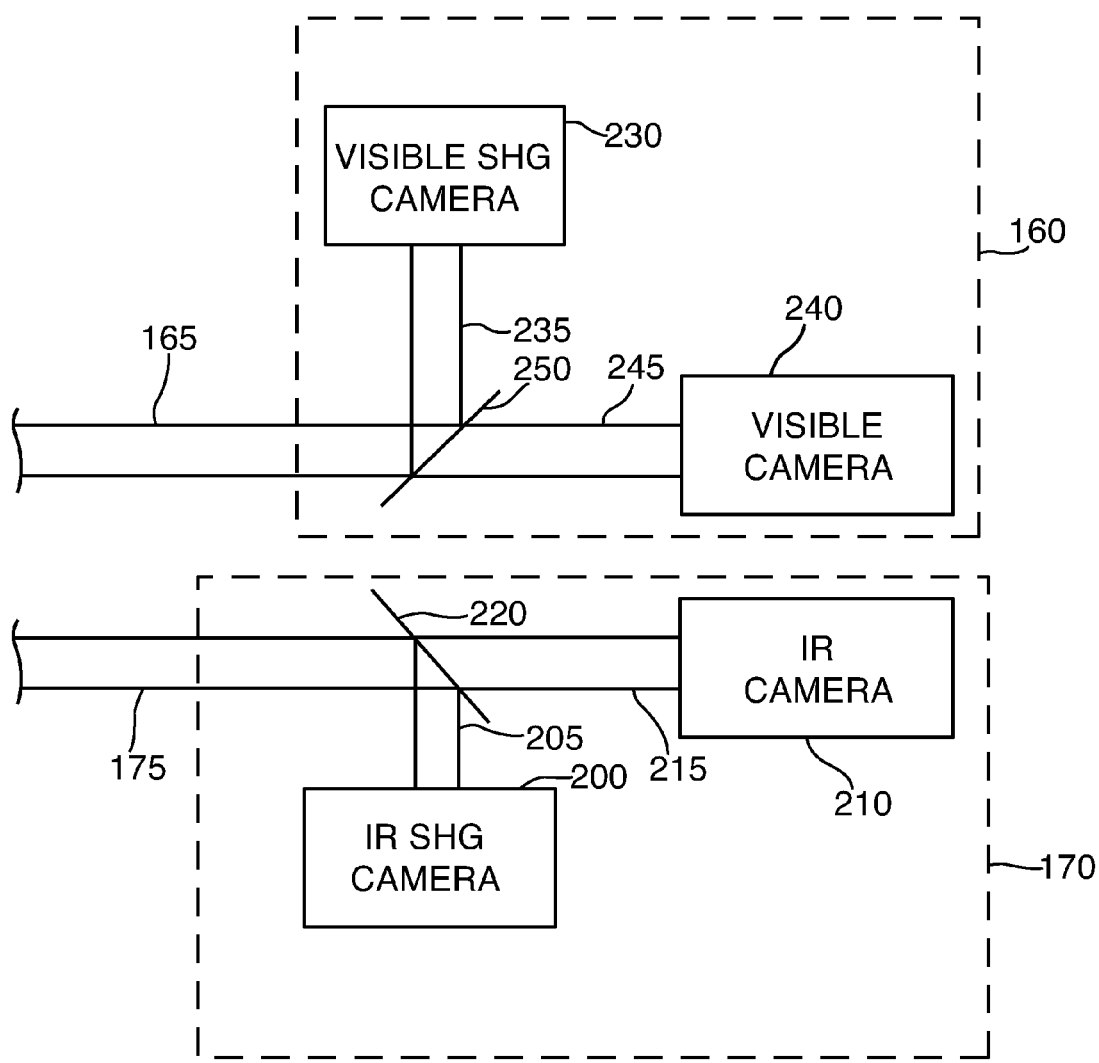
FIG. 2 is a block diagram showing the composition of the infrared light and visible light camera systems according to an aspect of the present disclosure.

System 100 in FIG. 1 also includes a number of cameras for detecting light reflected from the surface of article under test 105, including a Raman (third order) camera 140 which receives a light beam 145 and a sum-frequency camera 150 which receives a light beam 155. System 100 also includes paired visible and visible second harmonic generation (SHG) cameras 160 which receive a light beam 165, and paired IR and IR SHG cameras 170 which receive a light beam 175. Referring now to FIG. 2, the paired visible light and visible light second harmonic generation (SHG) cameras 160 include a visible light SHG camera 230 and a visible light camera 240 which are positioned to each receive light beam 165 via a beam splitter 250. In particular, beam splitter 250 is positioned to split light beam 165 into a first portion 235 that is provided to visible light SHG camera 230 and a second portion 245 that is provided to visible light camera 240. Similarly, the paired IR and IR second harmonic generation (SHG) cameras 170 include an IR SHG camera 200 and an IR camera 210 which are positioned to each receive light beam 175 via a beam splitter 220. In particular, beam splitter 220 is positioned to split light beam 175 into a first portion 205 that is provided to IR SHG camera 200 and a second portion 215 that is provided to IR camera 210. Each of the cameras 140, 150, 200, 210, 230 and 240 produces an output signal that is communicated in a conventional manner to a processor 180 in FIG. 1 via a link not shown in FIG. 1 for processing as discussed below.

As also discussed below, the reflected light beams 145, 155, 165 and 175 are at a particular angle with respect to the surface of device under test 105 based on the fixed angles that light beams 115, 125 and 135 are directed at the surface of device under test 105. The cameras 140, 150, 200, 210, 230 and 240 are thus positioned to receive such light beams. Each camera 140, 150, 200, 210, 230, 240 is a conventional detector as defined below with respect to FIG. 4.

As one of ordinary skill in the art will readily recognize, light sources 110, 120, 130 and cameras 140, 150, 200, 210, 230 and 240 may be fixed in place and article under test 105 may be moved so that the area 190 of the light beams 115, 125, 135 moves over the entire surface of article under test 105. In another embodiment, light sources 110, 120, 130 and cameras 140, 150, 200, 210, 230 and 240 may be mounted on a fixture that moves along the surface of article under test 105. In yet another embodiment, light sources 110, 120, 130 may be arranged to raster the respective output light beams 115, 125, 135 across the surface of the article under test 105, and the detectors 140, 150, 200, 210, 230 and 240 arranged to move proportionally to receive the respective associated return light beams 145, 155, 165, 175.

Figure 3:
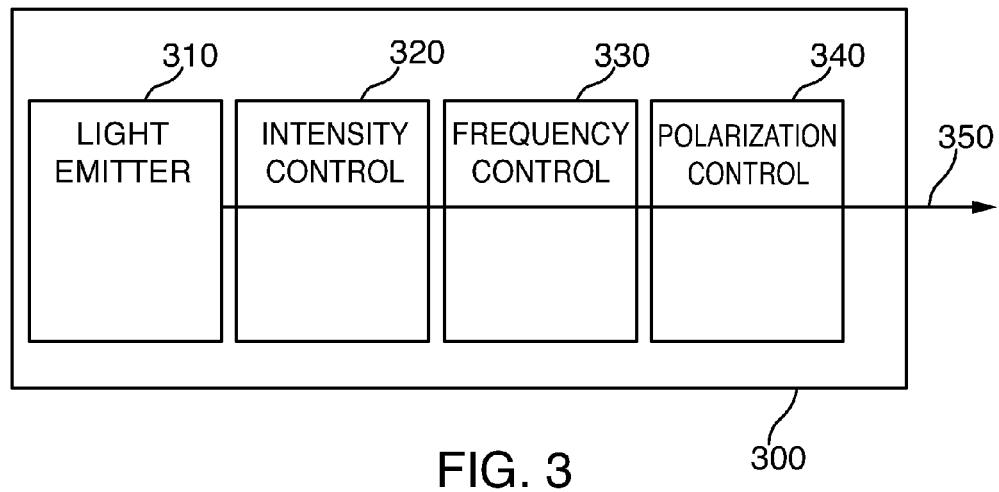
FIG. 3 is a block diagram showing the composition of the light sources according to an aspect of the present disclosure.

Referring now to FIG. 3, each of the light sources 110, 120, 130 is configured similarly, as shown by representative light source 300, but each may be configured for a different intensity, frequency and/or polarization. Light source 300 includes a light emitter 310, an intensity control 320, a frequency control 330 and a polarization control 340 for outputting a light beam 350. Light emitter 310 is preferably a narrow frequency bandwidth visible pulse laser and, may be, for example a pulsed diode laser, a continuous wave diode laser or a pulsed solid state laser or a continuous wave solid state laser. Intensity controls may include broadband filters for reducing intensity or may specifically refer to certain frequency notch filters which are intended to drop intensity levels where the detectors can act in a linear fashion. Frequency controls can be accomplished in simple cases by frequency dependent color filters or notch filters and in more elaborate by a spectrophotometer that is typically composed of a diffraction grating which operates at a frequency or bandwidth of interest. The key point for the frequency control is to ensure that only light in beam 350 is directed at the surface 105 and that stray light produced by light emitter 310 is removed, and as one of ordinary skill in the art will readily recognize, other frequency selective elements may also be used. Polarization control typically consists of two separate optical elements, a polarizer which only passes light of one polarization and a polarization modifying element—typically a halfway plate or a quarter wave plate. A halfway plate is used to rotate the polarization to the desired orientation. A quarter wave plate is used to change the polarization from linear to circular or from circular to linear as needed. As shown, the polarizer is the last element before light beam 350 leaves the source and heads for the surface 150. Each light source 110, 120, 130 is configured, based on the selection of light emitter 310, intensity control 320, frequency control 330 and polarization control 340 in each to provide a respective coherent beam of light 115, 125, 135.

Figure 4:
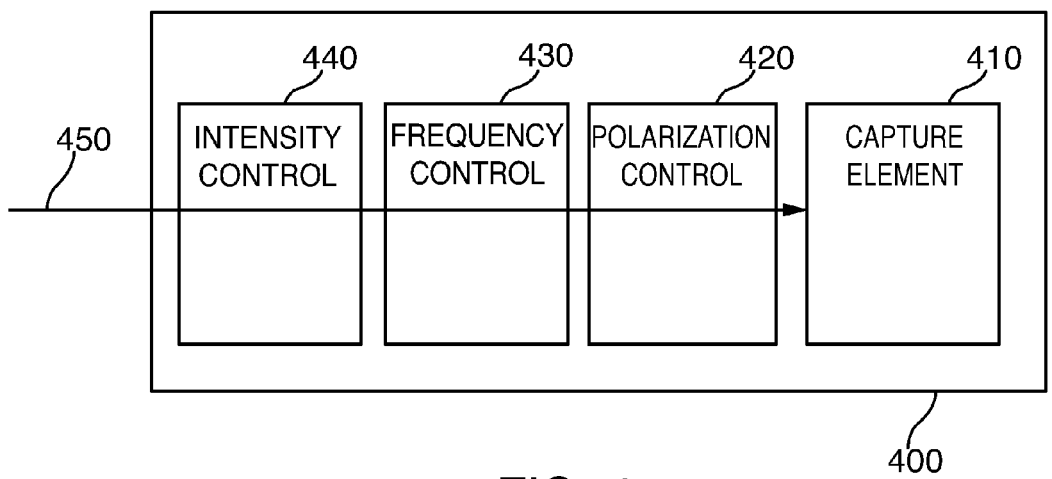
FIG. 4 is a block diagram showing the composition of the cameras according to an aspect of the present disclosure.

Referring now to FIG. 4, each of the cameras 140, 150, 200, 210, 230 and 240 is configured similarly, as shown by representative camera 400. Camera 400 includes a capture element 410, a polarization control 420, a frequency control 430 and an intensity control 440 for receiving light beam 450. Exemplary capture elements 34 include, without limitation, cameras, CCD devices, imaging arrays, photometers, and like devices. The frequency control 430 and intensity control 440 operate on light beam 450 in a similar manner as intensity control 320 and frequency control 330 operate on light beam 350 as discussed above. Preferably, polarization control 420 consists of a half wave plate and quarter wave combination, followed by a polarizer.

In operation, the system 100 shown in FIG. 1 provides a combination of linear infrared spectroscopy, second order surface frequency mixing spectroscopy, and third order nonlinear optics (e.g., Raman spectroscopy) spectroscopy. System 100 provides a number of ways of performing species identification and allows the cross correlation between the three types of spectroscopies in order to avoid false negative spectral features.

In particular, visible light source 120 and IR light source 110 are configured and positioned to provide light signals which allow the processor 180 to generate simultaneous linear (same frequency) and non-linear (second harmonic generation) real time spectroscopic signals, in conjunction with paired visible light and visible light second harmonic generation (SHG) cameras 160 and paired IR and IR SHG cameras 170. As one of ordinary skill in the art will readily recognize, paired visible light and visible light second harmonic generation (SHG) cameras 160 and paired IR and IR SHG cameras 170 are positioned at a particular predetermined angle to receive the appropriate respective return light signals 165, 175 from surface 105.

Further, visible light source 120 and IR light source 110 are also configured and positioned to provide light signals which allow the processor 180 to generate a sum-frequency ($\omega_{IR}+\omega_{VISIBLE}$) real-time spectroscopic signal, in conjunction with sum-frequency camera 150. As one of ordinary skill in the art will readily recognize, sum-frequency camera 140 is positioned at a particular predetermined angle to receive the appropriate return light signals 155 from surface 105.

Finally, visible light source 120 and visible light source 130 are configured and positioned to provide light signals which allow the processor 180 to generate a third-order ($2\omega_{VIS1}-\omega_{VIS2}$) (e.g., Raman) real-time spectroscopic signal, in conjunction with Raman (third order) camera 140. As one of ordinary skill in the art will readily recognize, Raman (third order) camera 140 is positioned at a particular predetermined angle to receive the appropriate return light signals 145 from surface 105.

The processor 180 is coupled to receive signals from each of cameras 140, 150, 200, 210, 230 and 240 and is configured to calculate in real time a linear spectroscopic signal, a second harmonic generation spectroscopic signal, a sum-frequency spectroscopic signal and a third order spectroscopic signal. The processor 180 is also configured to compare each calculated signal with each other calculated signal and with a predetermined baseline signal to ensure that the article under test conforms to an expected value. When the processor 180 determines that the calculated signals indicate that the article under test does not conform to the expected value, processor 180 provides a fault signal which may be used to halt formation of the part under test 105 for either repair thereof or so that part under test 105 may be immediately discarded.

Figure 5:
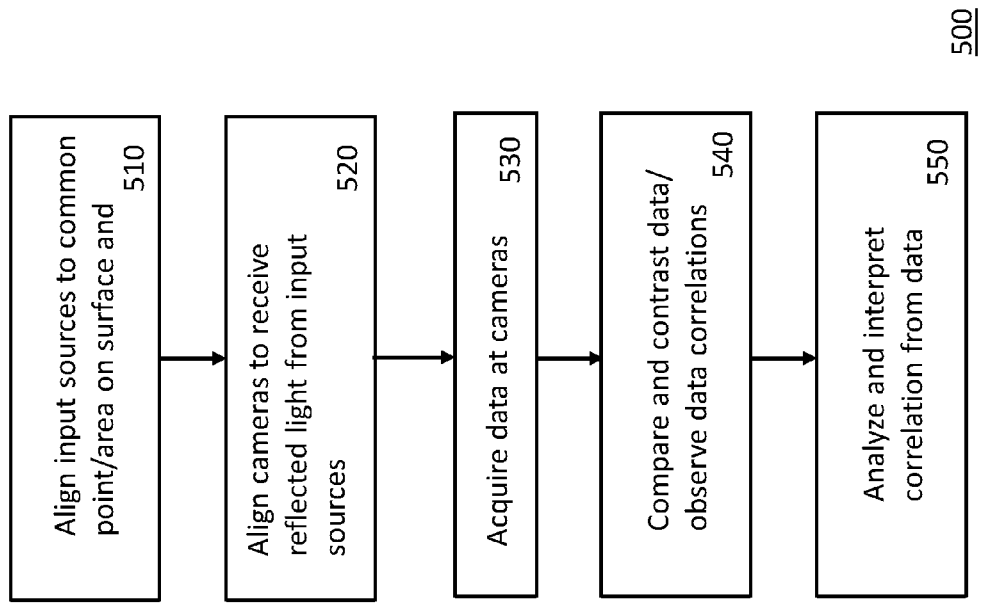
FIG. 5 is a flow chart of a method for operating the active real-time characterization system of the present disclosure.

Referring now to FIG. 5, a flow chart 500 of a method for operating the active real-time characterization system of the present disclosure is shown. In step 510, the input light sources are aligned to a common point or area on the surface of the article under test. Next, at step 520, the cameras are aligned to receive light reflected from the input sources. As evident from the discussion above, the third order camera 140, the sum-frequency camera 150, the visible light and visible light SHG cameras and the IR and IR SHG cameras are aligned separately. Further, at step 530, data is acquired at each of the cameras/detectors. After this, at step 540, the acquired data is compared and contrasted, and correlations among the data are observed. Finally, at step 550, the correlations among the data are analyzed and interpreted to determine whether or not the composition of the article under test falls within expected ranges.

As one of ordinary skill in the art will readily recognize, the active-real time characterization system 100 of the present disclosure may be applied to testing for composition of the article under test, for identifying contamination on the surface of the article under test or for a combination of both material composition and contamination identification. In addition, the active real-time characterization system 100 of the present disclosure may be used to test graphite fiber-based materials, polymer/plastic materials, glass fiber reinforcement-based materials such as fiberglass and glass laminate aluminum reinforced epoxy ("GLARE"), resins, plastics or polymers without reinforcement fibers, metals, and ceramics including glass materials.

By providing a combination of linear, non-linear, sum-frequency and third order real time spectroscopic signals, the present system provides the ability to more accurately monitor the chemistry of composite parts during formation by avoiding false negative spectral features. This system can allow, in some cases, defects to be repaired and thus prevent the loss of the composite part. In other cases, this system can ensure that production is halted as soon as a defect is identified, and thus preventing further costly work from being performed on a composite part destined to be discarded.

In further embodiments, the data generated by the active-real time characterization system 100 of the present disclosure may be combined for analysis with data separately generated by way of UV-VIS-NIR spectroscopy, IR spectroscopy, microwave spectroscopy, THz spectroscopy, ultrasonic NDE/NDI, Raman spectroscopy, Brillouin spectroscopy and/or ellipsometry.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. A system for providing active real-time characterization of an article under test, comprising:
    an infrared light source for outputting a beam of coherent infrared light, the infrared light source configured to direct the beam of coherent infrared light at a particular area on the article under test;
    a first visible light source for outputting a first beam of coherent visible light, the first visible light source configured to direct the first beam of coherent visible light at the same particular area on the article under test;
    a visible light second harmonic generation camera configured to receive a first predetermined return beam of light from the particular area on the article under test;
    an infrared second harmonic generation camera configured to receive a second predetermined return beam of light from the particular area on the article under test;
    a sum frequency camera configured to receive a third return beam of light from the particular area on the article under test; and
    a processor coupled to receive signals from the visible light second harmonic generation camera, the infrared second harmonic generation camera and the sum frequency camera, the processor configured to calculate in real time a linear spectroscopic signal, a second harmonic generation spectroscopic signal and a sum-frequency spectroscopic signal, the processor also configured to compare each calculated signal with each other calculated signal and with a predetermined baseline signal to ensure that the article under test conforms to an expected value.

2. The system of claim 1, further comprising:
    a second visible light source for outputting a second beam of coherent visible light, the second visible light source configured to direct the second beam of coherent visible light at the same particular area on the article under test;
    a third order camera configured to receive a fourth return beam of light from the particular area on the article under test; and
    wherein the processor is also configured to calculate in real time a third order spectroscopic signal and to compare the third order spectroscopic signal with the other calculated signals and with a predetermined baseline signal to ensure that the article under test conforms to an expected value.

3. The system of claim 1, wherein each of the sources includes an intensity control for setting a predetermined intensity for the respective output beam of light.

4. The system of claim 1, wherein each of the sources includes a frequency control for setting a predetermined wavelength for the respective output beam of light.

5. The system of claim 1, wherein each of the sources includes a polarization control for setting a predetermined polarization for the respective output beam of light.

6. The system of claim 1, wherein each of the cameras includes an intensity control for setting a predetermined intensity for the respective input beam of light.

7. The system of claim 1, wherein each of the cameras includes a frequency control for setting a predetermined wavelength for the respective input beam of light.

8. The system of claim 1, wherein each of the cameras includes a polarization control for setting a predetermined polarization for the respective input beam of light.

9. The system of claim 1, further comprising:
    a visible light camera configured to receive the first predetermined return beam of light from the particular area on the article under test; and
    a beam splitter configured to split a return beam of light into two portions, a first portion directed to the visible light camera and a second portion directed to the visible light second harmonic generation camera.

10. A system for providing active real-time characterization of an article under test, comprising:
    an infrared light source for outputting a beam of coherent infrared light, the infrared light source configured to direct the beam of coherent infrared light at a particular area on the article under test;
    a first visible light source for outputting a first beam of coherent visible light, the first visible light source configured to direct the first beam of coherent visible light at the same particular area on the article under test;

a visible light second harmonic generation camera configured to receive a first predetermined return beam of light from the particular area on the article under test;
an infrared second harmonic generation camera configured to receive a second predetermined return beam of light from the particular area on the article under test;
a third order camera configured to receive a third return beam of light from the particular area on the article under test; and
a processor coupled to receive signals from the visible light second harmonic generation camera, the infrared second harmonic generation camera and the third order camera, the processor configured to calculate in real time a linear spectroscopic signal, a second harmonic generation spectroscopic signal and a third order spectroscopic signal, the processor also configured to compare each calculated signal with each other calculated signal and with a predetermined baseline signal to ensure that the article under test conforms to an expected value.

11. The system of claim 10, further comprising:
a second visible light source for outputting a second beam of coherent visible light, the second visible light source configured to direct the second beam of coherent visible light at the same particular area on the article under test;
a sum frequency camera configured to receive a fourth return beam of light from the particular area on the article under test; and
wherein the processor is also configured to calculate in real time a sum frequency spectroscopic signal and to compare the sum frequency spectroscopic signal with the other calculated signals and with a predetermined baseline signal to ensure that the article under test conforms to an expected value.

12. The system of claim 10, wherein each of the sources includes an intensity control for setting a predetermined intensity for the respective output beam of light.

13. The system of claim 10, wherein each of the sources includes a frequency control for setting a predetermined wavelength for the respective output beam of light.

14. The system of claim 10, wherein each of the sources includes a polarization control for setting a predetermined polarization for the respective output beam of light.

15. The system of claim 10, wherein each of the cameras includes an intensity control for setting a predetermined intensity for the respective input beam of light.

16. The system of claim 10, wherein each of the cameras includes a frequency control for setting a predetermined wavelength for the respective input beam of light.

17. The system of claim 10, wherein each of the cameras includes a polarization control for setting a predetermined polarization for the respective input beam of light.

18. The system of claim 10, further comprising:
a visible light camera configured to receive the first predetermined return beam of light from the particular area on the article under test; and
a beam splitter configured to split a return beam of light into two portions, a first portion directed to the visible light camera and a second portion directed to the visible light second harmonic generation camera.

19. A method for active real-time characterization of an article under test, comprising the steps of:
directing an infrared light source and a first visible light source at an area on a surface of the article under test;
aligning a visible light second harmonic generation camera, an infrared second harmonic generation camera and a sum-frequency camera to receive light from the infrared light source and first visible light source reflected from the surface of the article under test;
acquiring data from each of the cameras based on the received light;
comparing and contrasting the data from each of the cameras and observing correlations among the data; and
analyzing and interpreting the correlations among the data to determine if the composition of the article under test is within expected ranges.

20. The method of claim 19, further comprising the steps of:
directing a second visible light source at the area on a surface of the article under test;
aligning a third order camera to receive light from the first visible light source and the second visible light source reflected from the surface of the article under test;
acquiring data from the third order camera; and
also using the data from the third order camera in the comparing and contrasting steps and analyzing and interpreting steps.

* * * * *